United States Patent
Schöni

[19]

[11] Patent Number: 6,072,319
[45] Date of Patent: Jun. 6, 2000

[54] DEVICE FOR MEASURING PROPERTIES OF A TEXTILE PRODUCT

[75] Inventor: Markus Schöni, Schwerzenbach, Switzerland

[73] Assignee: Zellweger Luwa AG, Switzerland

[21] Appl. No.: 09/215,309

[22] Filed: Dec. 18, 1998

[30] Foreign Application Priority Data

Dec. 19, 1997 [CH] Switzerland ............................ 2926/97

[51] Int. Cl.$^7$ .................................................. G01R 27/26
[52] U.S. Cl. ............................................ 324/671; 324/672
[58] Field of Search ..................................... 324/661, 663, 324/664, 671, 686, 690, 725, 672

[56] References Cited

U.S. PATENT DOCUMENTS

| | | | |
|---|---|---|---|
| 3,757,211 | 9/1973 | Goto | 324/61 R |
| 4,710,701 | 12/1987 | Strentz | 324/61 P |
| 5,042,299 | 8/1991 | Wells | 73/304 C |
| 5,304,937 | 4/1994 | Meyer | 324/686 |
| 5,394,096 | 2/1995 | Meyer | 324/686 |

FOREIGN PATENT DOCUMENTS

| | | |
|---|---|---|
| 2541261 | 3/1977 | Germany . |
| 1 448 061 | 10/1998 | Germany . |
| 1 805 146 | 2/1990 | Russian Federation . |
| 1 373 922 | 11/1974 | United Kingdom . |
| 1373922 | 2/1990 | United Kingdom . |

OTHER PUBLICATIONS

International Search Report for CH 292697 Dec. 19, 1997.

*Primary Examiner*—Josie Ballato
*Assistant Examiner*—V. Nguyen
*Attorney, Agent, or Firm*—Burns, Doane, Swecker & Mathis

[57] ABSTRACT

The disclosure relates to a device for measuring properties of a textile product in a measuring gap in which the textile product is inserted. On each of its surfaces the measuring gap has an electrode of a measuring capacitor, between which the product is inserted, an electrode of a compensation capacitor and a conductor. Disturbing influences can be effectively compensated by this arrangement.

8 Claims, 13 Drawing Sheets

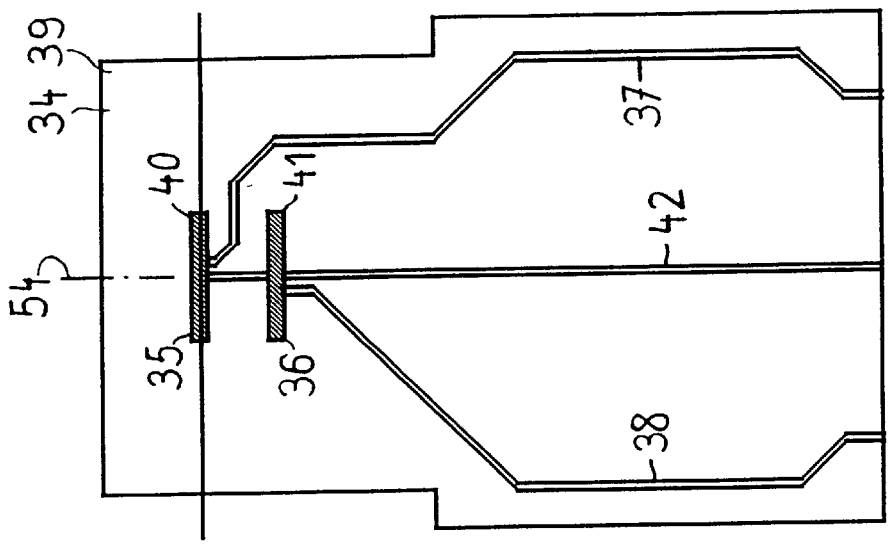
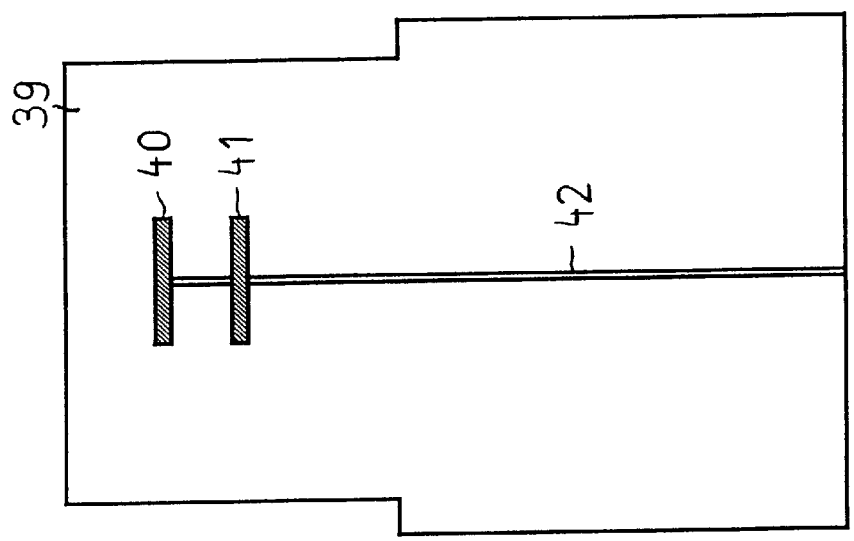
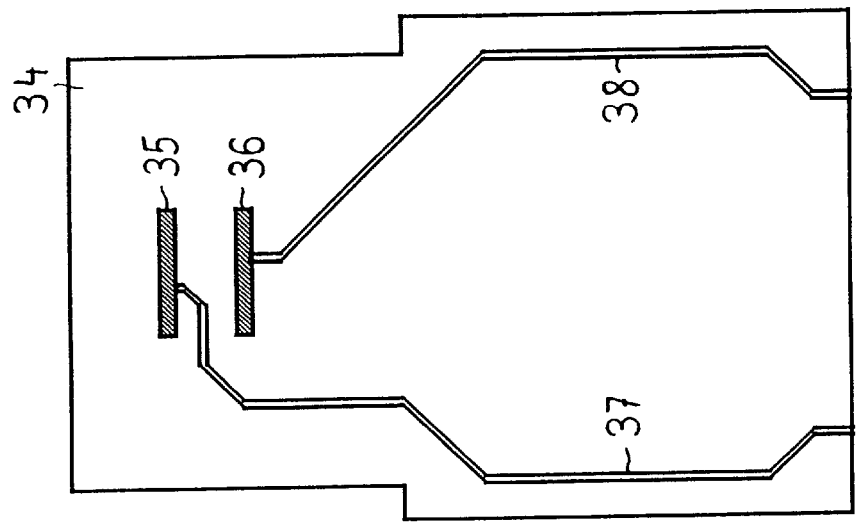

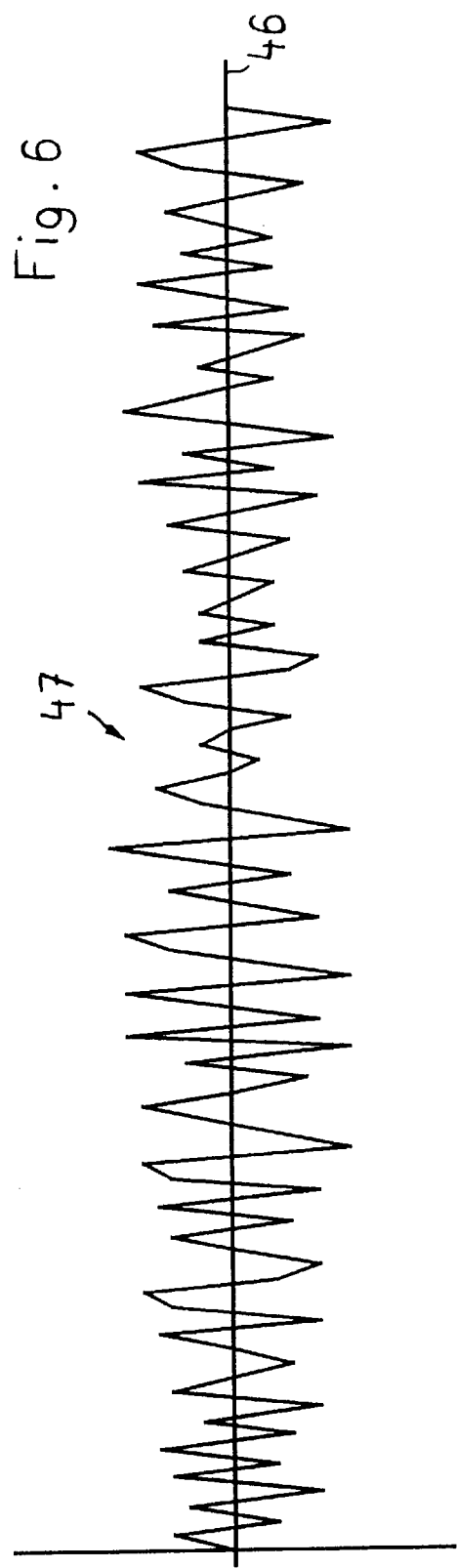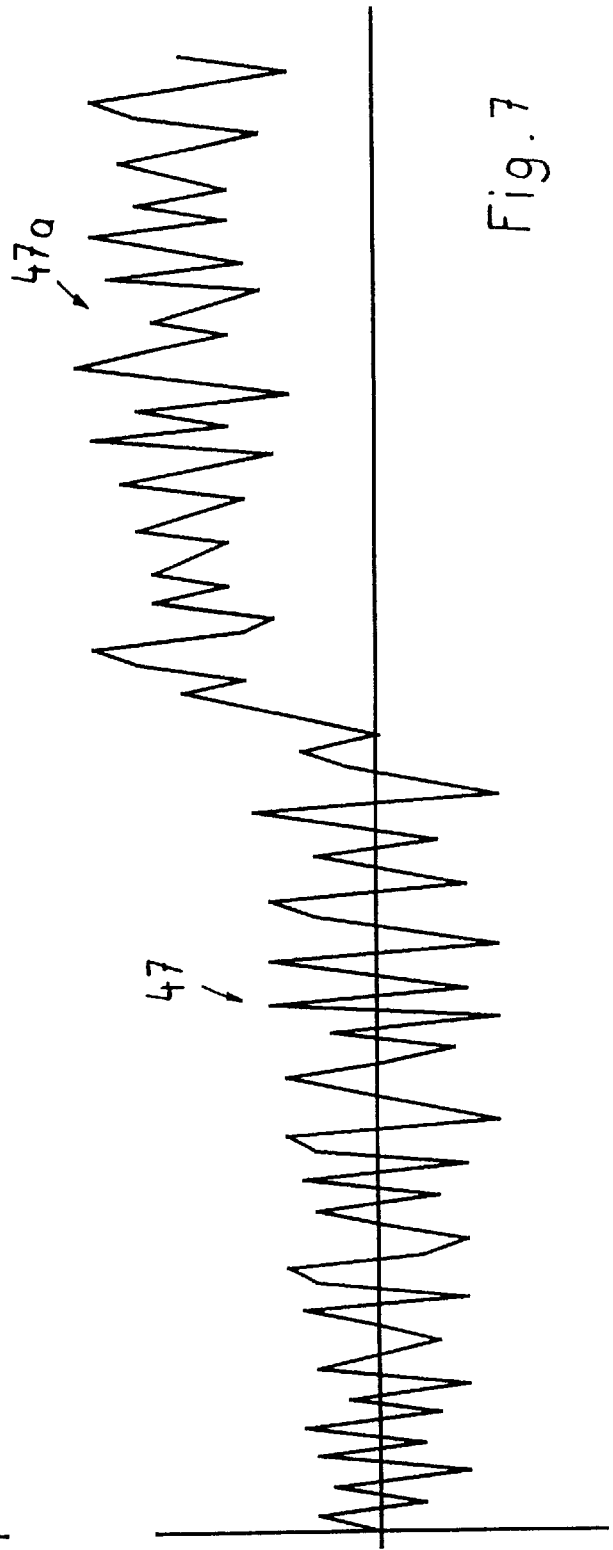

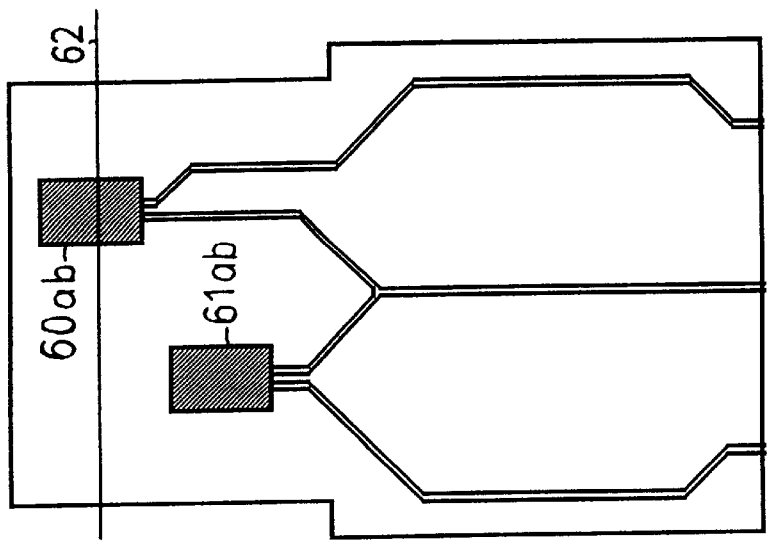
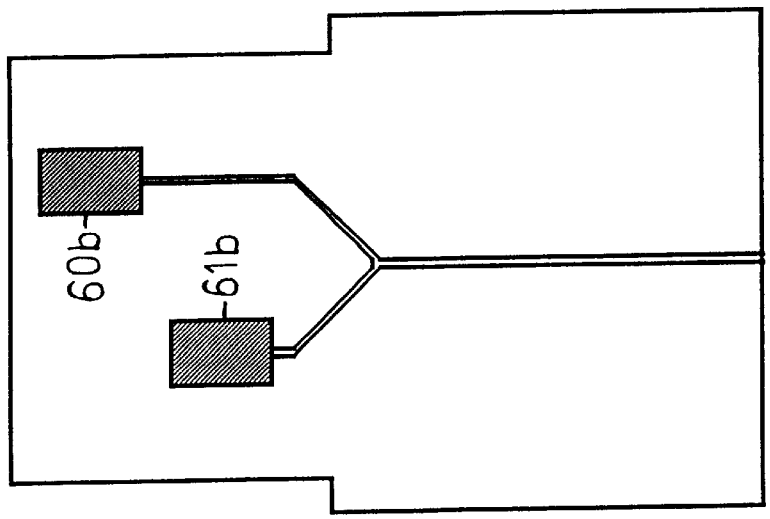
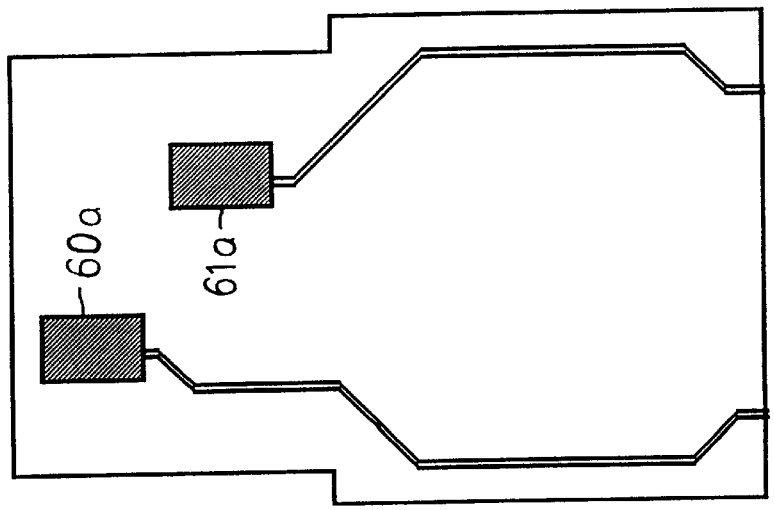

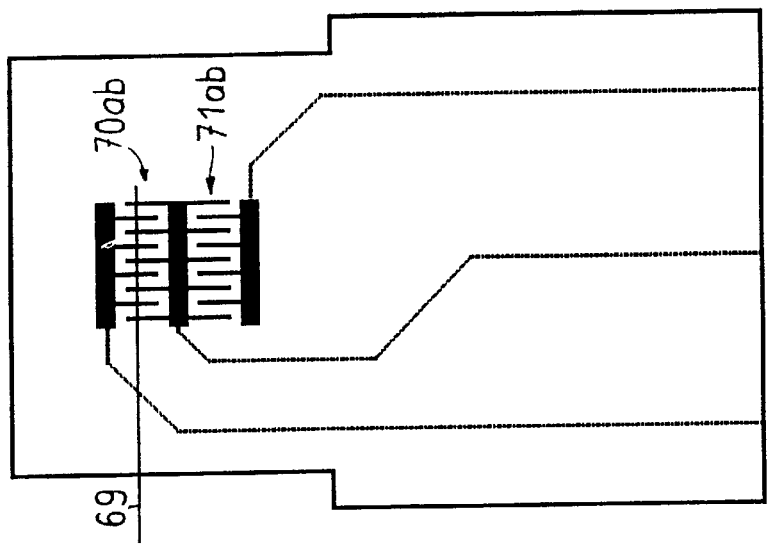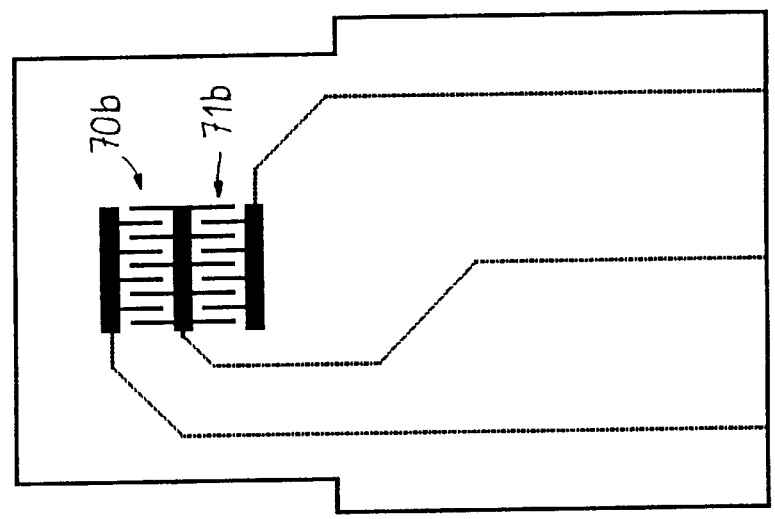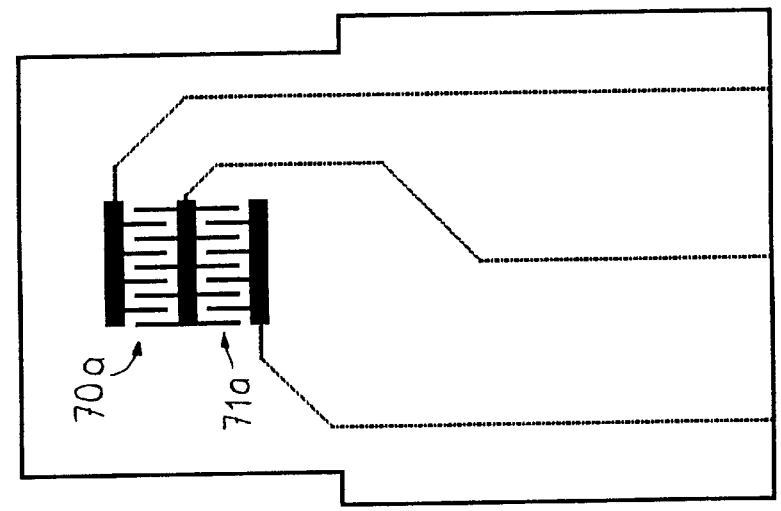

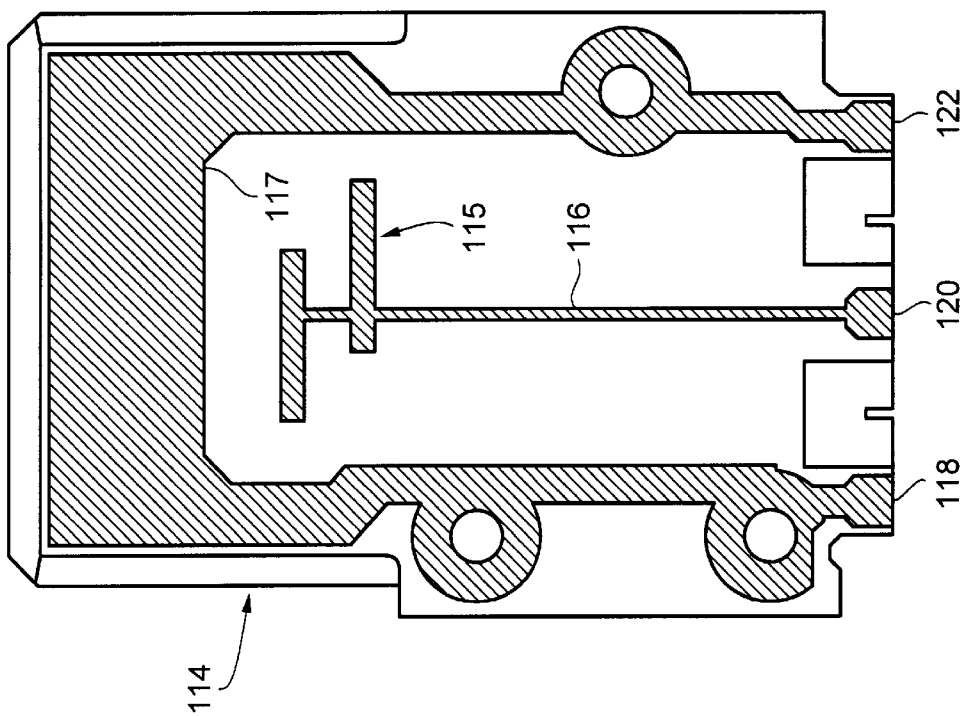
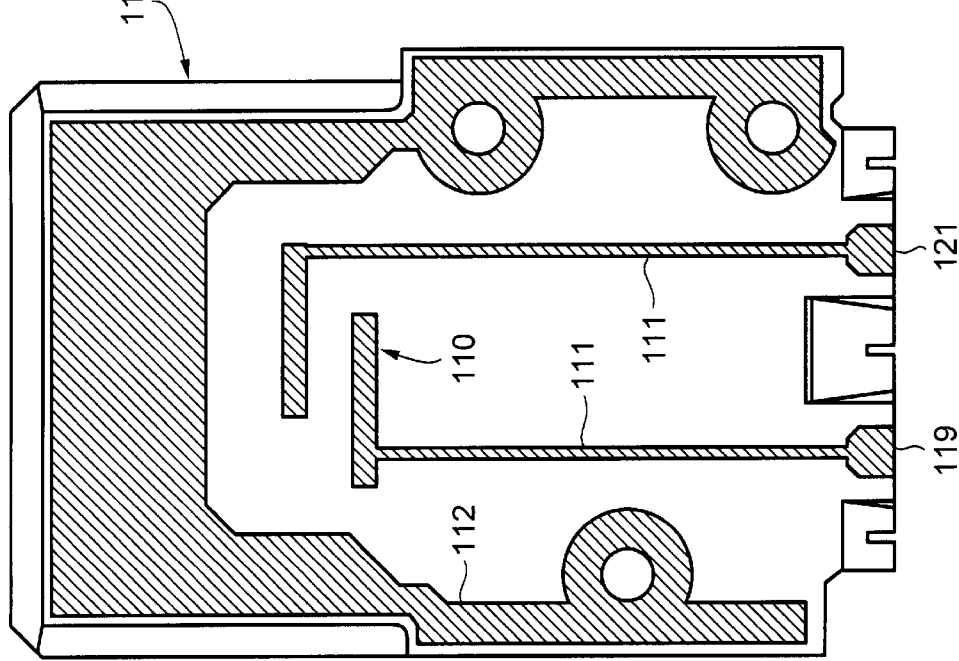

6,072,319

DEVICE FOR MEASURING PROPERTIES OF A TEXTILE PRODUCT

BACKGROUND OF THE INVENTION

The present invention relates to a device for measuring properties of a textile product disposed within a measuring gap.

One example of a textile product measuring device of this kind is disclosed in DE-A-36 21 324. In this device, two capacitors, a measuring capacitor and a compensation capacitor, are provided, both of which are connected to their own oscillator circuit and have their own gap between the electrodes or capacitor boards. The textile product is moved through the gap of the measuring capacitor, to measure the properties of interest. The gap of the measuring capacitor and the gap of the compensation capacitor are both provided with a device with which the width of the gap can be set. This device is designed in such a way that both gaps open or close to the same extent, so that the device can be set to different dimensions of textile products.

One limitation of this known device arises from the fact that the device for altering the distance between the boards of the two capacitors is very complicated and heavy. This device must operate sufficiently accurately to convert changes in the gap width on the measuring capacitor into a change in the gap width on the compensation capacitor as accurately as possible. This device cannot compensate for mechanical changes to the gap width which may take place inadvertently during the measurement. This also applies to other changes in the circumstances in the two gaps which do not take place simultaneously at both gaps, such as humidity changes in the measuring gap which are attributable to damp yarn and occur on a localized basis only.

A capacitive measuring head for yarn is disclosed in CH 551 007, in which a compensation capacitor is provided symmetrically and hence on each side of a measuring capacitor. The electrodes are much wider than the yarn so as to generate as uniform a field as possible in the measuring capacitor. To prevent interference fields, the connections or supply conductors to the electrodes of the measuring capacitor and the compensation capacitor are located in or behind the carrier material which holds the electrodes.

A disadvantage of this latter arrangement results from the fact that a relatively large area in the measuring head, and hence also in the measuring gap, is occupied by electrodes. In addition, the supply conductors to the electrodes, which are led towards and away from the electrodes in a direction perpendicular thereto, produce a structure which requires a great deal of space overall and is difficult to produce.

SUMMARY OF THE INVENTION

The present invention achieves the object of providing a measuring device which operates as accurately as possible, wherein the effects of changes in the width of the gap in the measuring capacitor are corrected in simple manner, and the electrodes and supply conductors are arranged in a space-saving manner.

This object is achieved by arranging a compensation capacitor to one side and in the same gap or measuring field as the measuring capacitor. The supply conductors to both capacitors are arranged in the same plane as the capacitors. Both capacitors are connected to a common evaluation circuit in which the measuring capacitance is compared with the compensation capacitance.

The advantages achieved by the invention can be seen in the fact that measurement errors which may arise because of changes in the gap width in the measuring capacitor, or because of differences in atmospheric humidity, temperature or air flow, are automatically compensated. The proposed solution requires no mechanically movable components and can easily be adapted to the specific circumstances in the measuring gap. As a result of its simplicity and space-saving arrangement, this solution may also be provided on devices with several measuring gaps. The adaptation of the measuring device to different dimensions may also be achieved, since measuring gaps of different widths are permanently provided and the textile product is guided into a measuring gap which is particularly suitable for it, according to cross-section.

The proposed solution also automatically ensures that the signal produced at the time of measurement does not drift as a result of disturbing influences. By appropriate arrangement of the different electrodes which make up the capacitors, it is easy to ensure that deformations which may be experienced by those surfaces which limit the measuring gap, and on which the electrodes are arranged, do not influence the measuring signal. Since the measuring electrode, the compensation electrode and the connections for them are all arranged on a common surface on both sides of the measuring gap, the metallization which forms these electrodes and connections on the surface may be applied to the surface very simply. This is possible, for example, by a screen-printing process or an etching process with no through-connections. This is advantageous in particular whenever the electrodes are arranged on ceramic bodies, as these can only be processed with great difficulty.

According to the invention, therefore, any number of measuring gaps may be produced by butt-mounting boards, e.g. ceramic boards, with electrodes on the surface in absolutely symmetrical manner. Parasitic capacitances are low in this case, which permits high measuring frequencies and produces low noise.

BRIEF DESCRIPTION OF THE DRAWINGS

The invention will be explained in greater detail below with the aid of an example and with reference to the accompanying drawings, in which:

FIGS. 3a to 3c show a first arrangement of capacitor electrodes, FIG. 6 shows an undisturbed signal, FIG. 7 shows a disturbed signal, FIGS. 9a to 9c show a fourth arrangement of capacitor electrodes, FIGS. 11a to 11c show a sixth arrangement of capacitor electrodes, FIG. 14 shows a perspective view of the back of the measuring device and FIGS. 15a, 15b show a further arrangement of elements.

DETAILED DESCRIPTION

Figure 1:
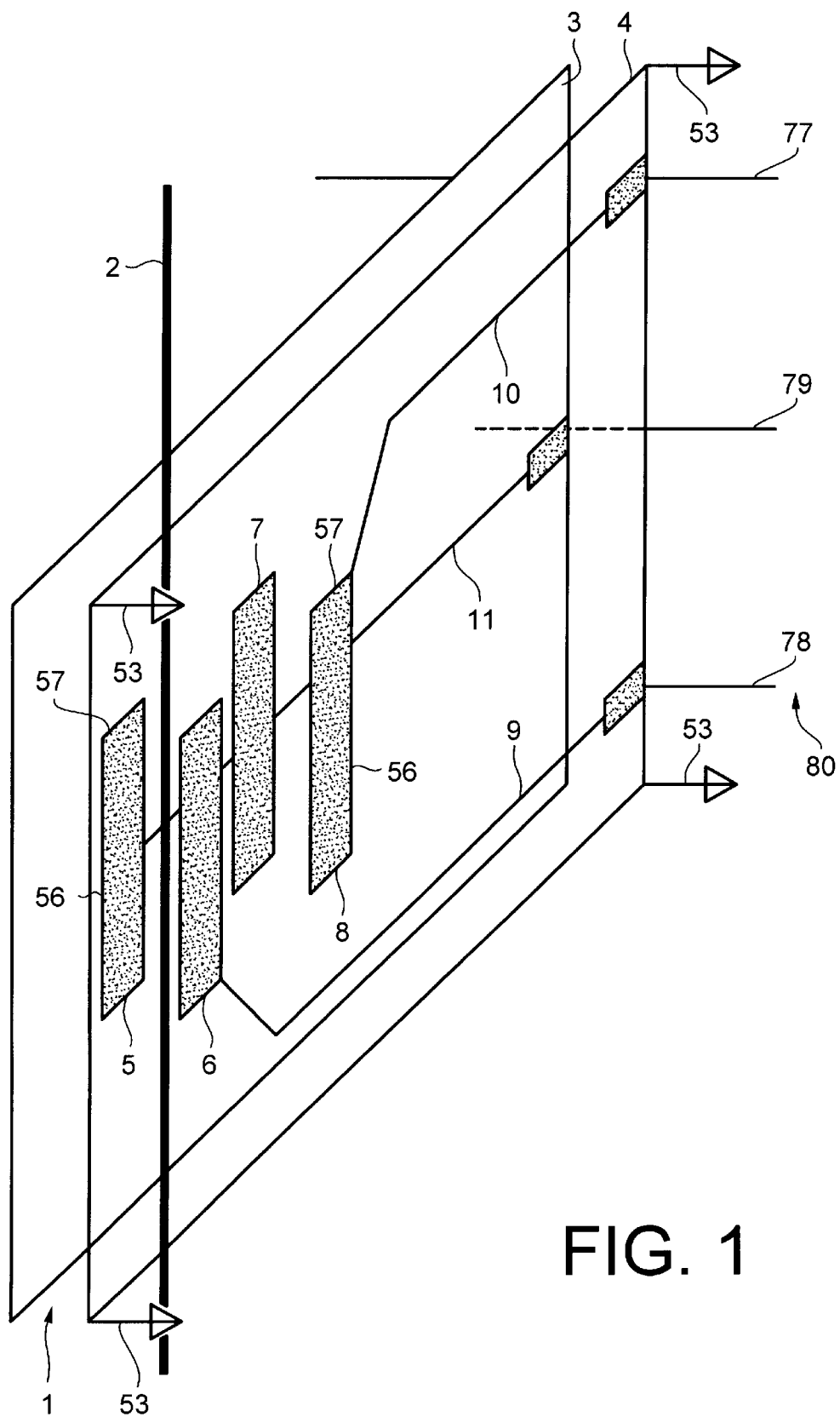
FIG. 1 shows the measuring device according to the invention in diagrammatic form.

FIG. 1 shows a diagrammatic view of a measuring gap 1 for a textile product 2 such as a sliver, a roving or a yarn. The measuring gap 1 is substantially defined by two surfaces 3 and 4. Electrodes 5, 6, 7 and 8 are formed on these surfaces 3 and 4. It is immaterial whether these electrodes 5 to 8 project or stand back slightly from the surfaces 3, 4. These electrodes 5, 6, 7, 8 are connected to further elements of a circuit, which are not shown, via a conductor 9, 10 of their own or via a common conductor 11. The electrodes 5 and 6 are arranged opposite each other in such a way that together they form a measuring capacitor. The electrodes 7 and 8 are arranged with respect to each other in such a way that they form a compensation capacitor. The textile product to be tested is guided, in a manner which is per se known and is therefore not shown in greater detail, in such a way that it lies between the electrodes 5 and 6 of the measuring capacitor and is optionally moved in its longitudinal direction. In so doing neither the electrodes 7, 8 of the compensation capacitor nor the conductors 9, 10 are shaded or covered by the product. In other words, the product is only disposed between the two electrodes 5 and 6. The electrodes 5, 6, 7, 8 of the capacitors each have a longitudinal side 56 and a narrow side 57. In an exemplary embodiment, the longitudinal sides of the electrodes 5, 6 of the measuring capacitor are at least approximately parallel to the longitudinal direction of the moving textile product 2. If one assumes, for example, that several measuring gaps are to be arranged adjacent to each other, then supply conductors 77, 78, 79 can be arranged in a transverse plane 80 for connection to several measuring capacitors and compensation capacitors in the same way.

Figure 2:
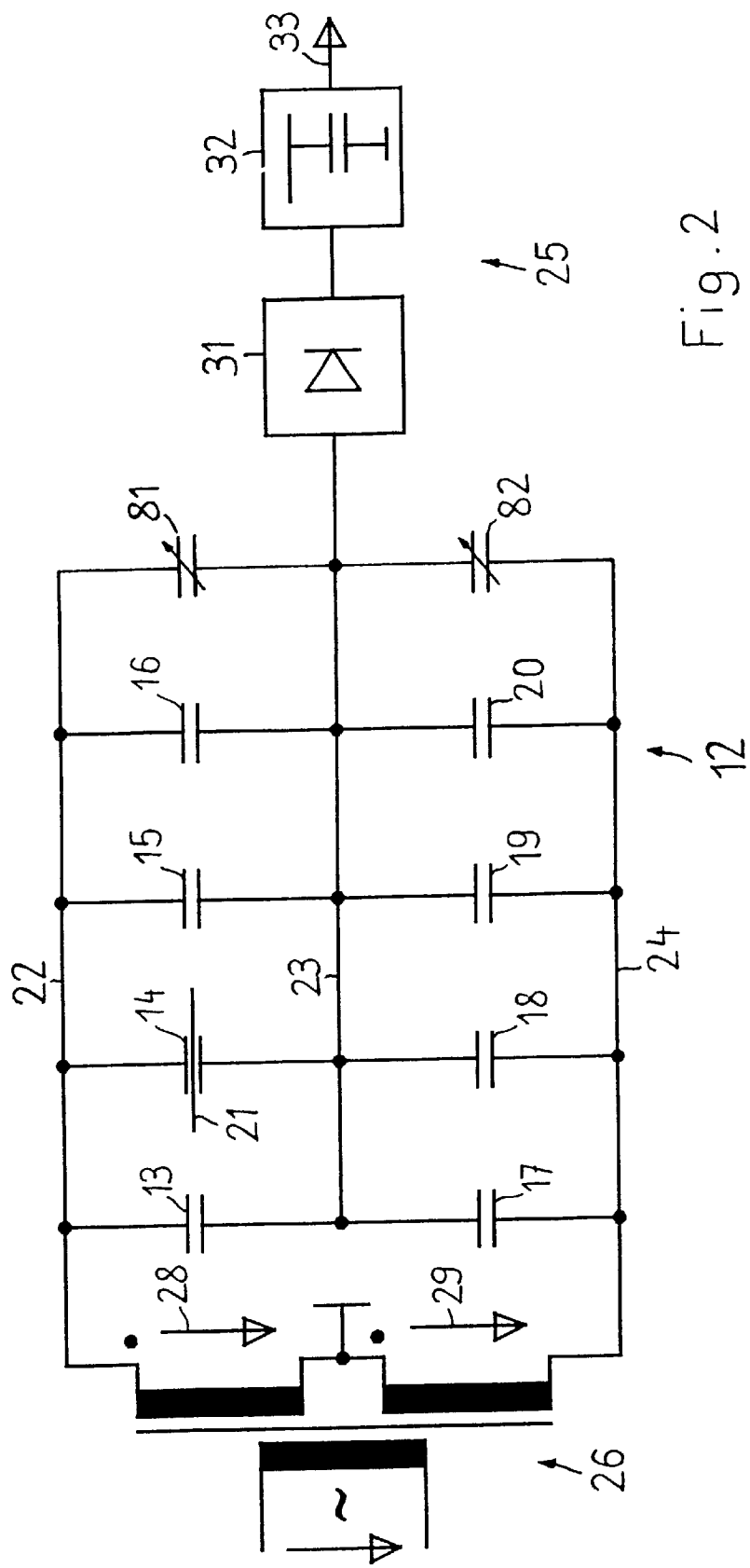
FIG. 2 shows a possible circuit arrangement for the measuring device.

FIG. 2 shows a possible circuit 12 for evaluating signals in connection with measuring capacitors and compensation capacitors of a type depicted in FIG. 1. Four measuring capacitors 13, 14, 15, 16 and four compensation capacitors 17, 18, 19, 20 and two tuning capacitors 81, 82 can be seen therein, for example. In this case only one measuring capacitor in each case is provided with a textile product 21, as is shown here for measuring capacitor 14.

Cooperating capacitor pairs 13–17, 14–18, 15–19 and 16–20 are connected in parallel, and connected to conductors 22, 23 and 24 which connect these capacitor pairs to an evaluation circuit 25 on the one hand and to a signal source 26 on the other hand. A sinusoidal oscillator which produces two signals in opposition or a.c. voltages 28 and 29 is provided as signal source 26, for example. The evaluation circuit 25 which is connected to capacitors 13 to 20 via the conductor 23 consists, for example, of a rectifier 31 and a filter 32 connected in series. A signal which reproduces properties of the measured product is thus available at output terminal 33. Together with two capacitors in each case, 13, 17 or 14, 18 etc., the signal source 26 forms a bridge circuit. The bridge circuit may also be designed in such a way that the capacitors 13 to 16 and the capacitors 17 to 20 together each form a branch of the bridge circuit.

FIG. 3a shows a diagrammatic top view of a surface 34 of a substrate, such as a printed circuit board, with an electrode 35 which belongs to the measuring capacitor and an electrode 36 which belongs to the compensation capacitor. Conductors 37 and 38 which lead to these electrodes can also be seen.

In corresponding manner FIG. 3b shows a surface 39 of another substrate which forms a measuring gap together with the above-mentioned surface 34. Electrodes 40 of the measuring capacitor and 41 of the compensation capacitor are connected via a common conductor 42 and connected to the remaining parts of the circuit.

FIG. 3c shows a superimposed view of the two surfaces 34, 39, which are opposite each other so that they form a measuring gap. The locations of the conductors 37, 38 and 42, is selected so that they are sufficiently far apart such that mutual influence remains low.

Figure 4C:
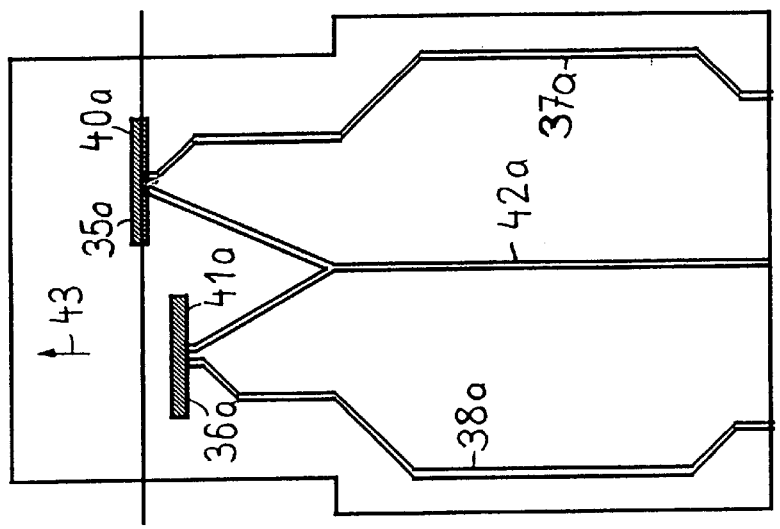
FIGS. 4a to 4c show a second arrangement of capacitor electrodes.
Figure 4B:
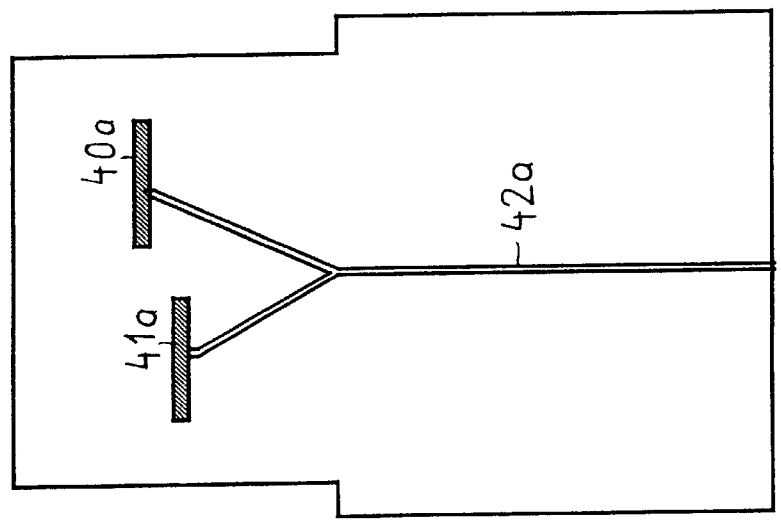
Figure 4A:
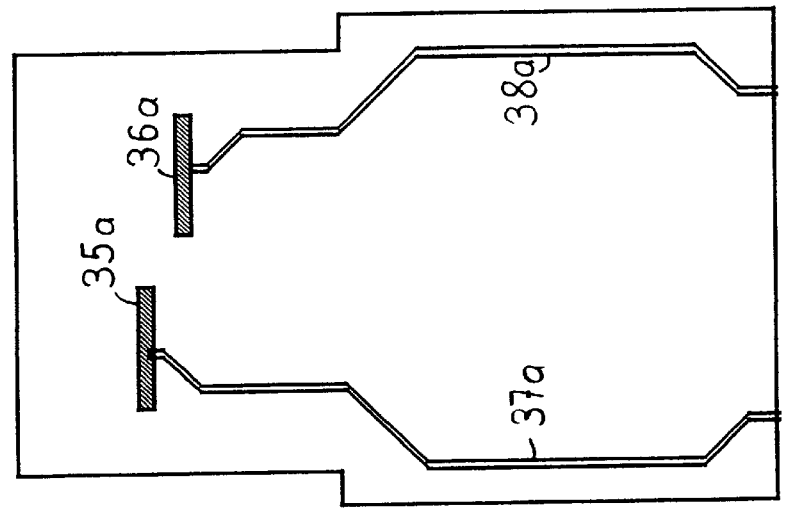

FIGS. 4a, 4b and 4c show a further arrangement of electrodes 35a, 36a, 40a, 41a and conductors 37a, 38a, 42a. The two electrode pairs 35a, 40a and 36a, 41a are arranged in such a way that when viewed in the direction of an arrow 43, they are as close to each other as possible but do not overlap.

Figure 5C:
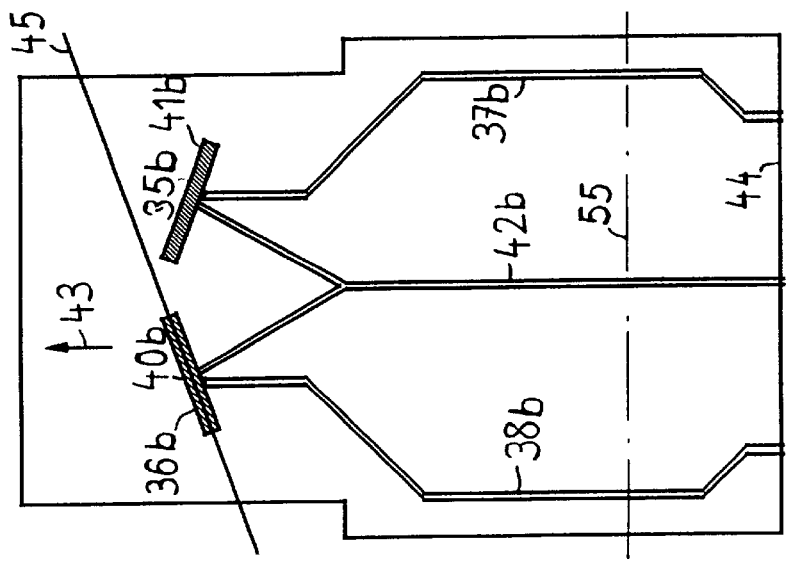
FIGS. 5a to 5c show a third arrangement of capacitor electrodes.
Figure 5B:
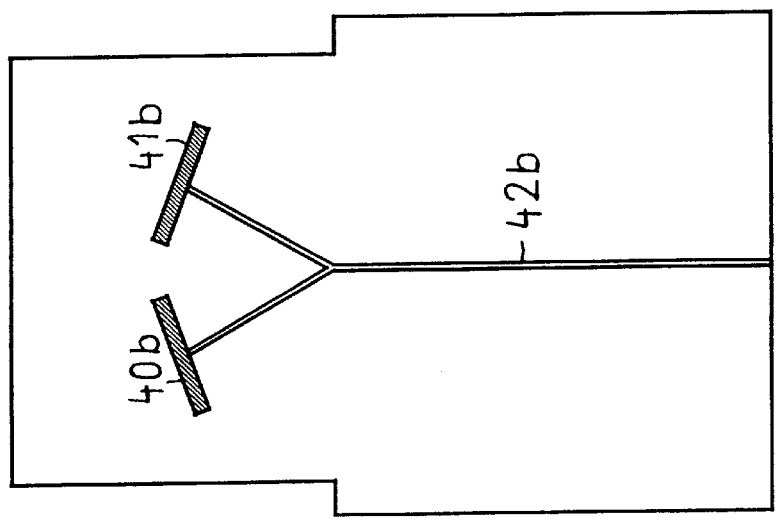
Figure 5A:
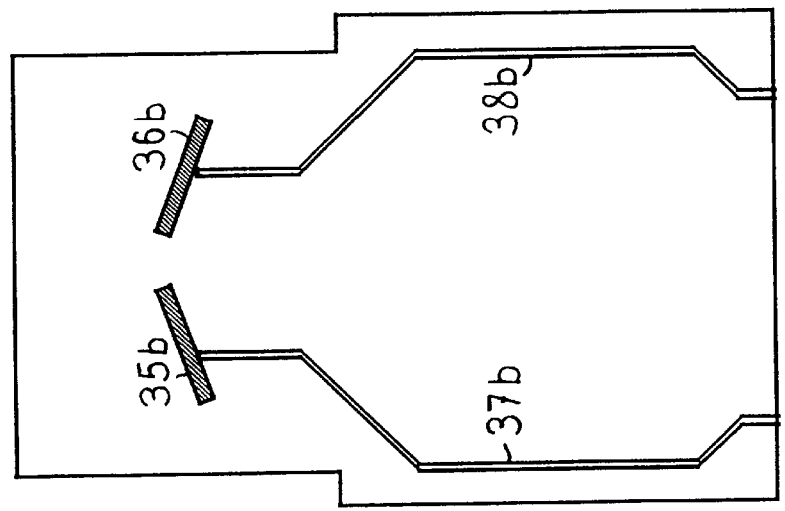

FIGS. 5a, 5b and 5c show a further arrangement of electrodes 35b, 36b, 40b, 41b and conductors 37b, 38b, 42b. The two electrode pairs 36b, 40b and 35b, 41b are arranged in such a way that, when viewed in the direction of an arrow 43, as far as possible they are at the same level or the same distance from a reference line 44 with respect to each other, but do not overlap. This also ensures that the product 45 does not come to lie between the electrodes 35b, 41b of the compensation capacitor, and this is, of course, also ensured in the embodiments described above.

FIG. 6 shows a signal 47 plotted against a time axis 46, whose deflections indicate properties of the product to be measured. Such a property may be the dimensions or cross-section of the product, for example. In this particular case, the signal 47 indicates departures of such properties from an average value as a function of time.

FIG. 7 shows a signal 47 of the type depicted in FIG. 6, but which has deflected in a region 47a as a result of external disturbing influences.

Figure 8:
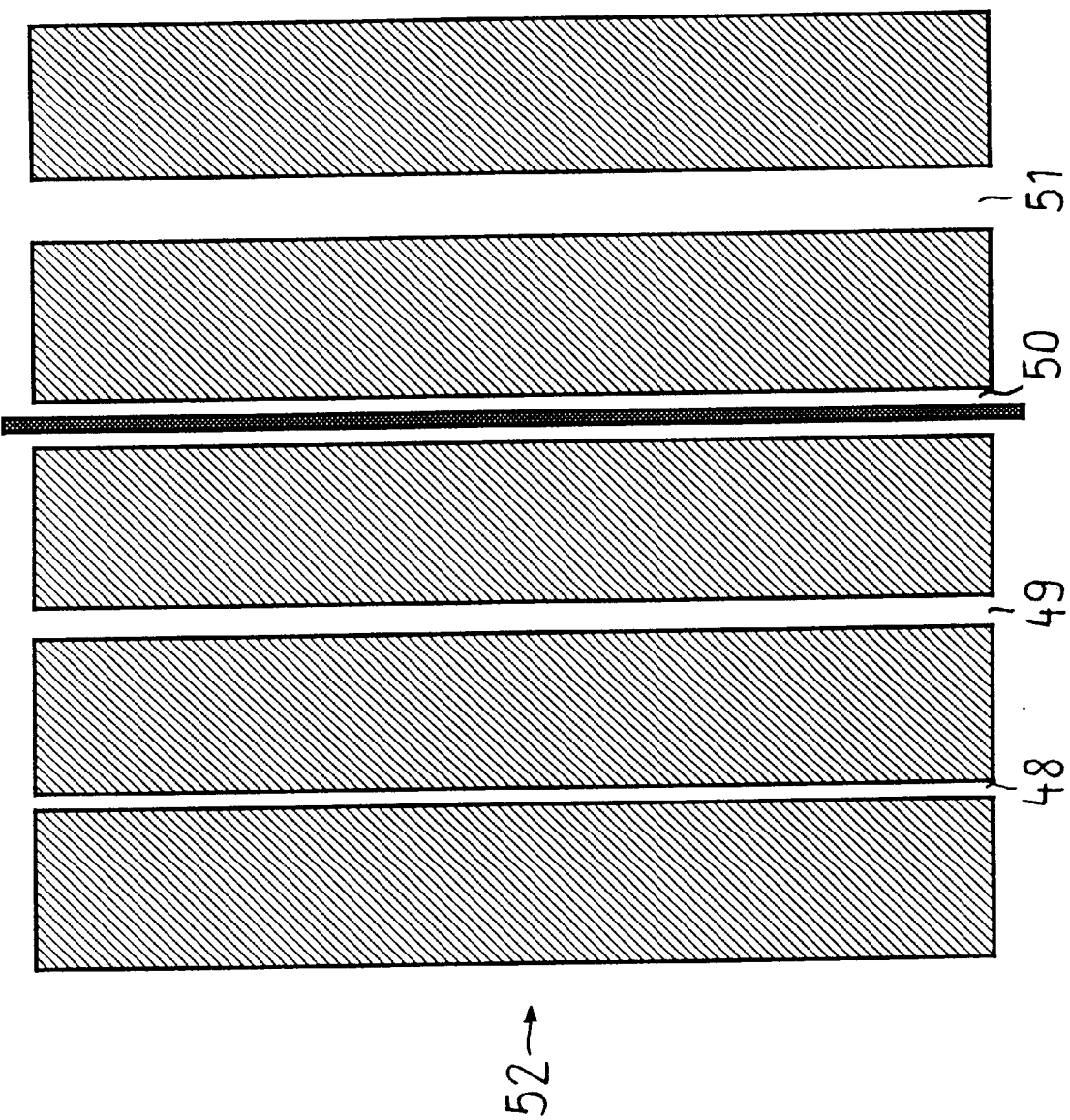
FIG. 8 shows a capacitor arrangement with several measuring gaps.

FIG. 8 shows a conceptual arrangement of several measuring gaps 48, 49, 50 and 51 of different widths which are commonly arranged in a single element 52. Each measuring gap is suitable for measuring products with different dimensions. Thick products are measured in measuring gap 51, thin products in measuring gap 48.

FIGS. 9a, 9b, 9c show further diagrammatic views of electrodes 60a, 60b and 60ab in superimposed position, which form a measuring capacitor, and electrodes 61a, 61b and 61ab which form a compensation capacitor. In this case the electrodes do not extend in the longitudinal direction of the product 62, but rather are transverse thereto. The product can thus assume different positions and no longer needs to he guided as accurately as was the case in the embodiments shown above. Or, other, thicker products such as rovings or slivers may be measured.

Figure 10C:
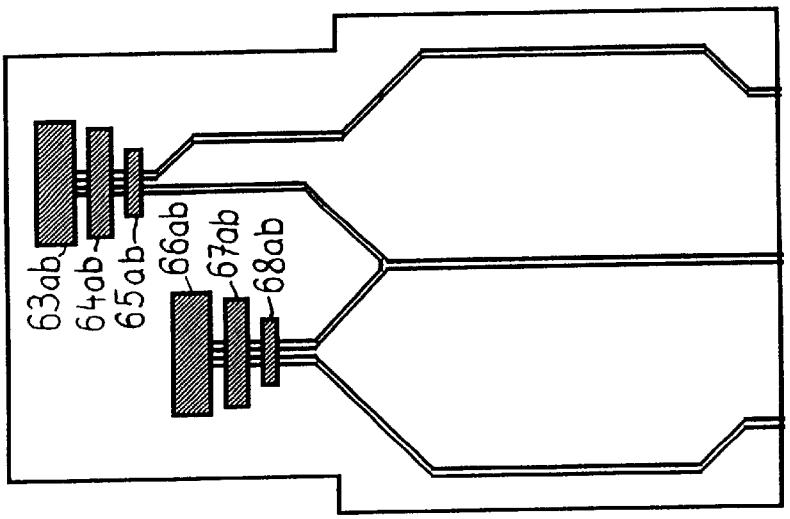
FIGS. 10a to 10c show a fifth arrangement of capacitor electrodes.
Figure 10B:
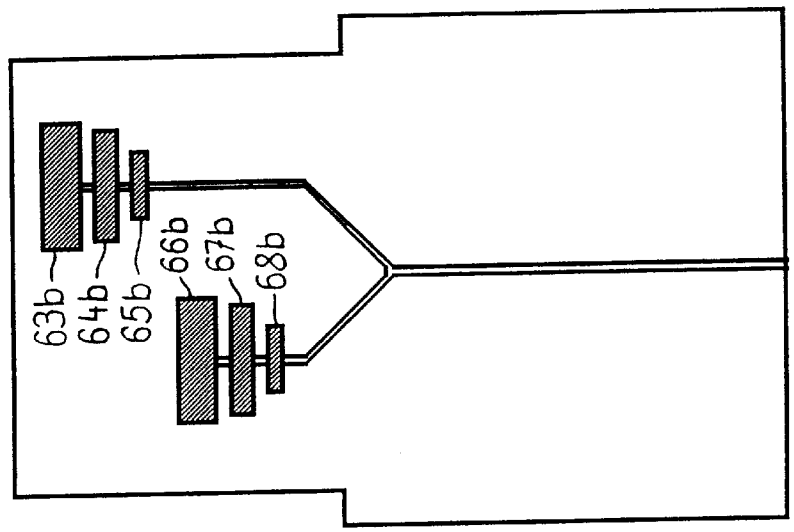
Figure 10A:
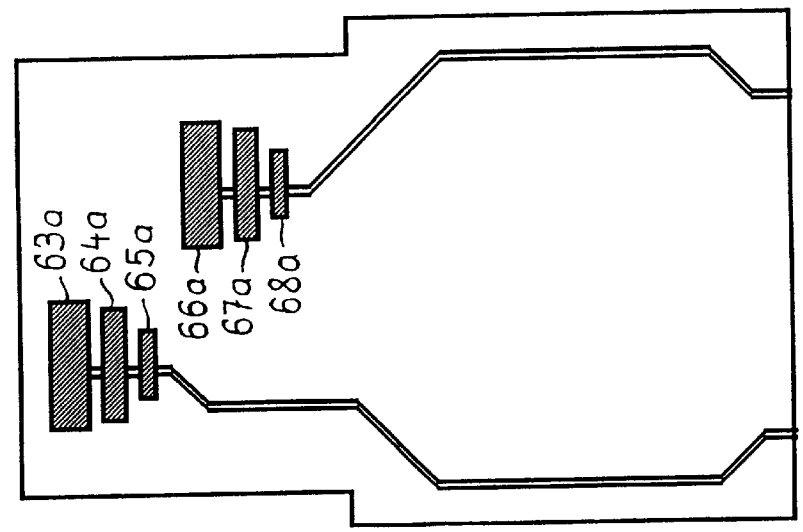

A further embodiment is shown in FIGS. 10a, 10b and 10c, in which three electrodes 63a, 64a and 65a, and 63b, 64b, 65b, for three measuring capacitors are arranged alongside each other. Electrodes 66a, 67a, 68a and 66b, 67b and 68b for compensation capacitors are correspondingly arranged alongside each other. The electrodes 63 are chiefly suitable for thicker products whereas the electrodes 65 are suitable for thin products. Three measuring capacitors and three corresponding compensation capacitors are thus arranged in one measuring gap. Additionally it is also conceivable to graduate the width of the measuring gap correspondingly so that it is wider in the region of the electrodes 63 than in the region of the electrodes 65.

A further possibility is shown in FIGS. 11a, 11b and 11c. In this case electrode fields 70a and 70b for a measuring capacitor for a product 69 and electrode fields 71a and 71b for a compensation capacitor are provided. In this case the. electrical fields no longer run transverse to the product as in the arrangements shown above, but lengthwise thereto.

Figure 12:
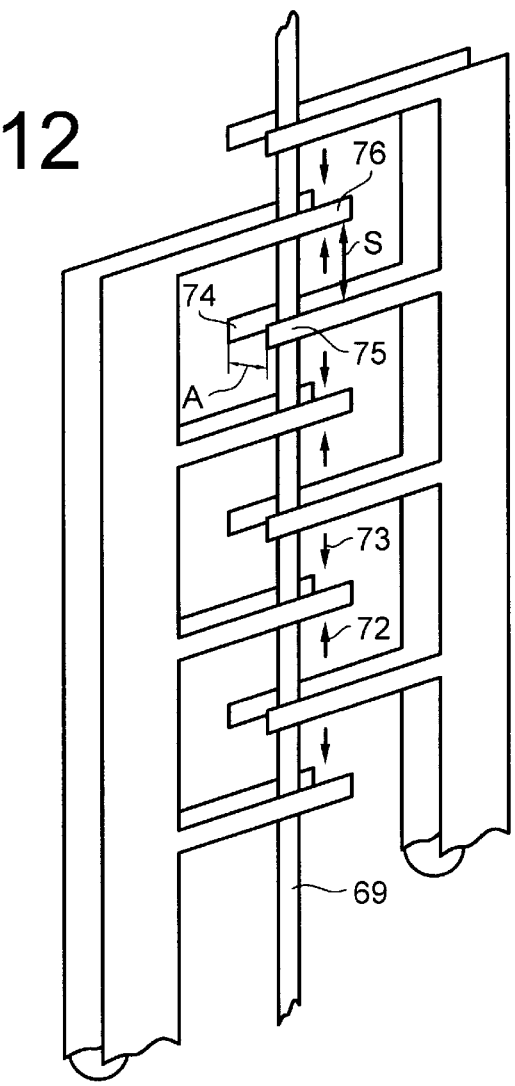
FIG. 12 shows a perspective view of the electrodes of the sixth arrangement.

This can be seen in particular from FIG. 12 which shows a perspective view of a capacitor with such electrode fields. The product 69 and field lines running parallel thereto and indicated by arrows 72 and 73 can be seen. To obtain as uniform a field as possible, the conductive pattern is applied not only to one board but two boards are used, as with cross-field sensors, wherein the same conductive pattern is opposed on both boards. Unlike the cross-field sensor, the sensitivity is determined not by the gap distance A between the legs 74 and 75, but by the leg distance S between legs 75 and 76 of the same conductive pattern or electrode field. In this sensor the drift may be particularly greatly improved with the compensation field as the capacitances are very small and there is therefore great sensitivity to disturbing influences.

Figure 13:
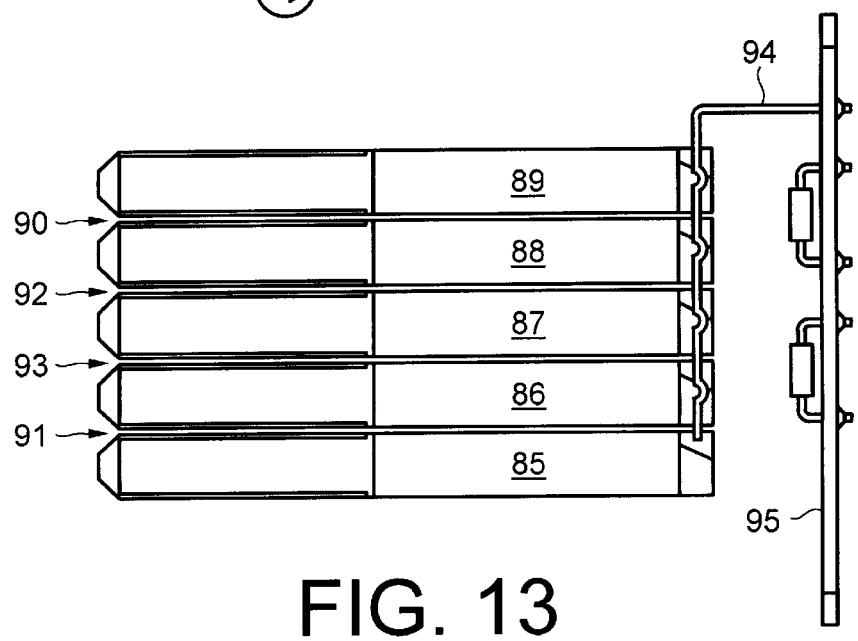
FIG. 13 shows a part of the measuring device.

FIG. 13 shows an arrangement of five carrier boards 85, 86, 87, 88 and 89, which form four measuring gaps 90, 91, 92 and 93 of different gap width, as depicted in FIG. 8. Preferably the measuring gaps 90 and 91 with the larger gap widths are arranged on the outside and the measuring gaps 92, 93 with the smaller gap widths on the inside. The electrodes in the measuring gaps 90 to 93 are connected via conductors, only one of which, conductor 94, is visible here, to a circuit board 95 on which the elements of the bridge circuits or the circuit shown in FIG. 2 are arranged, for example.

Figure 14:
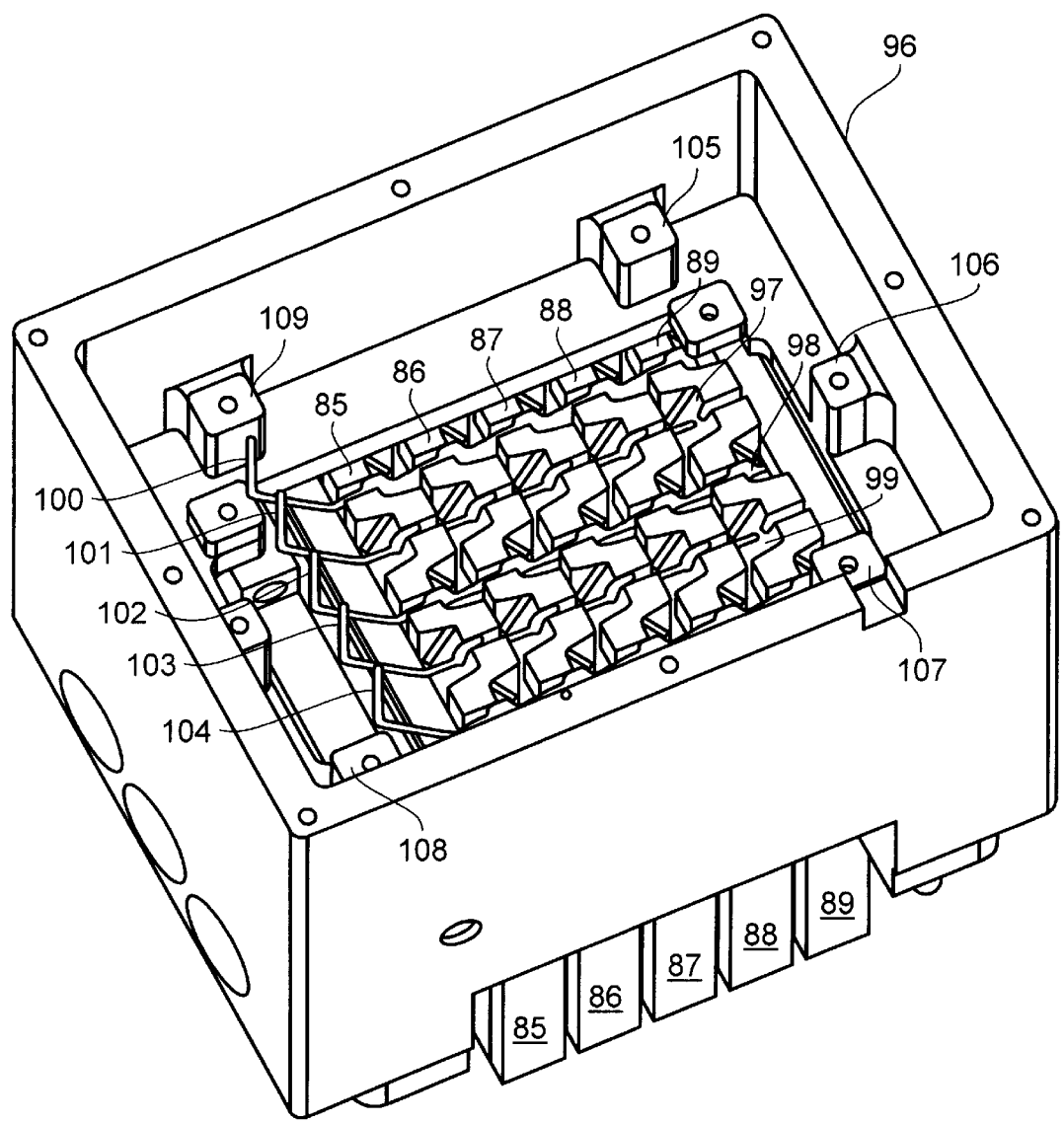

FIG. 14 shows the arrangement of the carrier boards 85 to 89 according to FIG. 13 in a housing 96 from the back. On its rear face each of these carrier boards 85 to 89 has several recesses 97, 98 and 99 along a part of a lateral surface on which the electrodes 5, 6, 7, 8 and conductors 9, 10, 11 according to FIG. 1 are arranged. This creates an access for a soldering instrument with which supply conductors 100, 101, 102, 103, 104 may be connected. The supply conductors 101–103 correspond, for example, to the conductors 22, 23, 24 of FIG. 2. Supply conductors 100 and 104 are provided for screens, discussed below. The circuit board 95 shown in FIG. 13 may be fixed in the housing 96 on supports 105 to 109.

FIG. 15a shows a view of a carrier board 113 on which a screen 112 is arranged in addition to electrodes 110 and conductors 111. Fib. 15b shows a carrier board 114 with corresponding electrodes 115 which form capacitors with the electrodes 110, a conductor 116 and a screen 117.

Connections 118 to 122 are connected to conductors 100 to 104 according to FIG. 14. The screens shield the measuring field in the capacitors from external disturbing influences on the one hand, and on the other hand ensures that the measuring field does not carry disturbances to the outside.

The mode of operation of the device according to the invention is as follows:

Two a.c. voltages 28 and 29 (FIG. 2) which are of the same value but in opposition, i.e., 180° out of phase, are generated with a transformer or an oscillator. With the bridge compensated and no test material 21, the measuring capacitors 13 to 16 have the same values as the compensation capacitors 17 to 20. There is therefore no voltage at the conductor 23. If the test product 21 is inserted into a measuring gap, the balance between the measuring capacitors and the compensation capacitors changes and an a.c. voltage is generated in the conductor 23, the amplitude of which is proportional to the mass of the product between the measuring electrodes. After rectification and filtering in the rectifier 31 and filter 32, a signal 33 is obtained whose form over time corresponds to the envelope of the a.c. signal in the conductor 23 and which thus corresponds to the dimensional form of the test material when it is moved through the measuring gap. This signal is shown in FIG. 6.

Disturbing influences may, however, be neutralized by the arrangement according to the invention. An example of a disturbing influence of this kind is the mechanical displacement of the surfaces 3 and 4 which form the measuring gap 1 or differing atmospheric or humidity conditions. If the measuring gap 1 widens as a result of mechanical or thermal load in the direction of arrows 53 (FIG. 1), the density of the electrical field between the electrodes 5 and 6 decreases and a test product 2 produces a smaller signal than when the electrodes 5 and 6 were in the original position. Since the electrodes 5 and 6 are connected to a circuit according to FIG. 2, however, the status of the field between the electrodes 5 and 6 alone is not critical. Rather, the status between the electrodes 5 and 6 relative to the status between the electrodes 7 and 8 is critical. This relative status does not change if the electrodes 7 and 8 are moved away from each other to the same degree as the electrodes 5 and 6. Under such conditions, the zero point does not move.

It is also conceivable that the two surfaces 3 and 4 are not displaced in a parallel manner due to the disturbing influences. In such a case, they no longer occupy a parallel position because of the disturbing influence. In this case the absolute value of the signal 47 may indeed undergo a change, but it will still remain centred to some extent. Special arrangements of the electrodes may take particular account of such events in any case. For example, the embodiment according to FIG. 3 is particularly suitable for compensating a twist of the one surface with respect to the other surface about an axis 54. In contrast, the embodiment according to FIG. 5 is particularly suitable for compensating a twist of the one surface about an axis 55.

The solution according to the invention is particularly advantageous in an arrangement of several measuring gaps 48 to 51 alongside each other, as shown in FIG. 8. The electrodes of these measuring gaps 48 to 51 may all be arranged in a common circuit and be connected together. If the measuring gap 50 is reduced for some reason, for example, the probable consequence will be that one of the adjacent measuring gaps 49 or 51 will enlarge correspondingly. In the circuit according to FIG. 2 this means, for example, that the gaps in the capacitors 14 and 18 are reduced, but the gaps in the capacitors 13 and 17 or 15 and 19 are correspondingly enlarged. It will easily be seen from this that the zero point does not move. By arranging the conductors at least approximately in a plane with the electrodes and by arranging the compensation capacitors on one side only, i.e. asymmetrically with respect to the test material, a very compact measuring head may be constructed. Preferably the surfaces of the boards which form a measuring gap are covered and protected by means of a coating, e.g. a glass coating, so that the metallizations which form the electrodes and supply conductors may be produced in a correspondingly thin-layered manner.

The same behaviour is also exhibited in the case of other disturbing influences such as temperature differences between the individual measuring gaps, humidity differences, other air flows or deterioration of the material.

With the solution according to the invention it is also conceivable to provide a single measuring gap whose surfaces 3 and 4 can be set with respect to each other by any mechanism in the direction of the arrow 53 (FIG. 1) in such a way that products of the most varied thicknesses can be measured therein. The gap of the compensation capacitor is correctly set automatically.

Similarly, other evaluation circuits may be provided. Such a circuit is disclosed, for example, in patent application DE 36 21 324. The measuring capacitance is always compared with the compensation capacitance, be it directly or by converting the capacitance into another physical magnitude such as a voltage, frequency or current.

What is claimed is:

1. A device for measuring properties of a textile product, comprising:

first and second substrates spaced from one another to define a gap between them within which the textile product is disposed;

a measuring capacitor comprised of first and second electrodes on opposed surfaces of said first and second substrates, respectively, and respective conductors disposed on said surface for connecting said electrodes to a signal source; and a compensation capacitor comprised of first and second electrodes on said opposed surfaces of said first and second substrates, respectively, and respective conductors disposed on said surfaces for connecting said electrodes to said signal source.

2. The device of claim 1 wherein the electrode of the measuring capacitor and the electrode of the compensation capacitor on one of said first and second substrates share a common conductor.

3. The device of claim 1 wherein said first and second substrates are movable relative to one another to vary said gap.

4. The device of claim 1 wherein the electrodes of said measuring capacitor are oriented at an inclined angle relative to the electrodes of said compensation capacitor.

5. The device of claim 1 wherein the textile product is elongated, and the electrodes of said measuring capacitor are elongated and oriented parallel to the textile product.

6. The device of claim 1 wherein the textile product is elongated, and the electrodes of said measuring capacitor are elongated and oriented transverse to the textile product.

7. The device of claim 1 comprising a multiplicity of said substrates disposed parallel to one another at different spacings to form plural gaps of different respective widths, each having a measuring capacitor and a compensation capacitor.

8. The device of claim 7 wherein the measuring capacitors of said plural gaps are connected parallel to one another, the compensation capacitors of said plural gaps are connected parallel to one another, and the measuring capacitors and compensation capacitors are connected to said source to form a bridge circuit.

* * * * *